(12) United States Patent
Palani

(10) Patent No.: US 9,962,088 B2
(45) Date of Patent: May 8, 2018

(54) NON-INVASIVE DIAGNOSTIC DEVICE BASED ON AUDIOMETRIC ANALYSIS

(71) Applicant: Rajesh Palani, Dharmapuri (IN)

(72) Inventor: Rajesh Palani, Dharmapuri (IN)

( * ) Notice: Subject to any disclaimer, the term of this patent is extended or adjusted under 35 U.S.C. 154(b) by 54 days.

(21) Appl. No.: 14/786,989

(22) PCT Filed: May 5, 2014

(86) PCT No.: PCT/IN2014/000301
§ 371 (c)(1),
(2) Date: Oct. 26, 2015

(87) PCT Pub. No.: WO2014/192017
PCT Pub. Date: Dec. 4, 2014

(65) Prior Publication Data
US 2016/0106318 A1     Apr. 21, 2016

(30) Foreign Application Priority Data
May 7, 2013   (IN) ............................ 2038/CHE/2013

(51) Int. Cl.
*A61B 5/00*       (2006.01)
*A61B 9/00*       (2006.01)
*A61B 5/08*       (2006.01)
*A61B 5/02*       (2006.01)
*A61B 7/00*       (2006.01)
*A61B 7/04*       (2006.01)

(52) U.S. Cl.
CPC .......... *A61B 5/0051* (2013.01); *A61B 5/0022* (2013.01); *A61B 5/02* (2013.01); *A61B 5/08* (2013.01); *A61B 5/4244* (2013.01); *A61B 5/4306* (2013.01); *A61B 5/7282* (2013.01); *A61B 5/742* (2013.01); *A61B 7/003* (2013.01); *A61B 7/04* (2013.01); *A61B 9/00* (2013.01)

(58) Field of Classification Search
CPC ....... A61B 5/0048; A61B 9/00; A61B 5/0051; A51B 8/44; A51B 9/00
See application file for complete search history.

(56) References Cited

U.S. PATENT DOCUMENTS

| 4,177,798 | A | * | 12/1979 | Leveque | .............. | A61B 5/0051 600/587 |
| 2004/0096803 | A1 | * | 5/2004 | Huang | ................. | A61B 5/1111 433/150 |
| 2005/0014999 | A1 | * | 1/2005 | Rahe-Meyer | ............ | A61B 5/01 600/323 |
| 2009/0312638 | A1 | * | 12/2009 | Bartlett | .................... | A61B 5/00 600/443 |

(Continued)

FOREIGN PATENT DOCUMENTS

| EP | 1486169 A2 | * | 12/2004 | ............. A61B 5/029 |
| JP | 09271475 A | * | 10/1997 | |
| JP | 10057379 A | * | 3/1998 | |

*Primary Examiner* — Daniel J Colilla

(57) ABSTRACT

The handheld device is useful in the diagnosis of diseases and medical conditions based on audiometric analysis of resonated sound. This device has a mechanism to create a sound with the particular characteristics, a mechanism to transmit the sound into the human body at the given anatomical surface area, a system to pick up or receive the resonated sound, an audiometric analyzer and a display to display the results based on the audiometric analysis of resonated sound.

6 Claims, 10 Drawing Sheets

(56) References Cited

U.S. PATENT DOCUMENTS

2010/0279262 A1\* 11/2010 Lecat ................. A61B 7/00
 434/266
2014/0235964 A1\* 8/2014 Banet ............. A61B 5/02055
 600/301

\* cited by examiner

| S. No | TB (Units in dB) | Normal (Units in dB) |
|---|---|---|
| 1 | -28 | -20 |
| 2 | -28 | -20 |
| 3 | -29 | -16 |
| 4 | -28 | -20 |
| 5 | -27 | -19 |

Table - 1

FIG. 6A

| S. No | Normal f in HZ | TB f in HZ |
|---|---|---|
| 1 | 562 | 656 |
| 2 | 562 | 656 |
| 3 | 562 | 656 |
| 4 | 562 | 656 |
| 5 | 468 | 656 |
| 6 | 281 | 656 |
| 7 | 281 | 656 |
| 8 | 468 | 843 |

Table - 2

FIG. 6B

NON-INVASIVE DIAGNOSTIC DEVICE BASED ON AUDIOMETRIC ANALYSIS

TECHNICAL FIELD

When a sound is transmitted into the human body, the resonated sound depends on the underlying medical condition. The following specification describes the invention of a hand held device that will help in the diagnosis of all the possible medical conditions and diseases based on the audiometric analysis of resonated sound upon transmitting a standardized sound with the particular characteristics into the human body. Further, this specification describes the invention of a hand held device that will help in diagnosis and epidemic screening of respiratory diseases including tuberculosis in Human Beings. The invention is also further related to creating and transmitting the standard percussion sounds on the specified area of human body, and differentiating the subjects with pulmonary tuberculosis of both sputum positive and sputum negative from the normal subjects based on the analysis of audiometric variations of resonated sounds. However for the audiometric analysis, ultrasound is not considered in this invention but uses the audible sound that can be resonated and picked up using a microphone and/or a diaphragm that can be placed firmly on the surface of the human body for audiometric analysis.

BACKGROUND OF THE INVENTION

When a sound is transmitted into the human body, the resonated sound depends on the underlying medical condition. There are many medical conditions and diseases that can be diagnosed based on the audiometric analysis of the resonated sound. One such disease is tuberculosis which is explained here.

Tuberculosis is a deadly, chronic, infectious disease which is generally caused by *Mycobacterium tuberculosis*. It is also the leading cause of death in patients infected with HIV. It is a bigger problem in many developing countries, with about 9.5 million new cases and 3 million deaths each year. India has the highest burden of this disease with about 2 million new cases a year.

Presently tuberculosis is diagnosed based on examination of sputum sample under the microscope, or by culturing the sample. A chest x ray may also help in the diagnosis. Recently Gene Xpert technique is used to diagnose this deadly disease. However, the microscope exam is not 100% reliable; sputum culturing is time consuming and takes weeks to get the result. Although Gene Xpert is capable of producing the results in minutes, it is very expensive and not commonly available. Also the above mentioned diagnostic tools do not come handy as a hand held device.

Also in the developing countries there is a need for the cost effective, improved, quicker, handy diagnostic and screening tool that will help in the diagnosis and epidemic screening of tuberculosis. The proposed invention fulfils this need and further provides related advantages.

Although percussion technique for some diseases is manually performed by some clinicians as a part of the clinical examination, it has its own limitations mainly due to limited human abilities and skills. This invention overcomes these limitations and also includes all other possible medical conditions and diseases that can be diagnosed based on the accurate audiometric analysis of resonated sounds.

Although in some diagnostic devices ultrasound is used, this invention does not use ultrasound.

OBJECTS OF THE INVENTION

An object of this invention is to propose a handheld device that will help in the diagnosis of diseases and medical conditions based on audiometric analysis of resonated sound.

A further object of this invention is to propose a diagnostic handheld device that will help in the diagnosis and/or epidemic screening respiratory diseases including pulmonary tuberculosis.

Also the further object of this invention is to propose a diagnostic handheld device which is economical and easy to handle.

A still further object of this invention is to propose a diagnostic handheld device based on the analysis of audiometric variations of different resonance sounds obtained from normal subjects and subjects with pulmonary tuberculosis of both sputum positive and sputum negative and related conditions like pneumonia.

Another object of this invention is to propose a diagnostic handheld device which can be used in epidemic screening of tuberculosis.

Still another object of this invention is to propose a diagnostic handheld device which helps in fast detection of tuberculosis.

Yet in another object of this device is to propose a diagnostic device which is non-invasive.

Yet another object of this invention is to propose the modified version of this device (hereafter called Percusogram) that is capable of analysing the percussion sounds and creating the audiometric graphs (hereafter called Percusograph) of the percussion sounds and also be able to print these graphs that will help in the diagnosis of tuberculosis and related conditions like pneumonia.

Yet still another object of this invention is to propose a diagnostic device which can be used in telemedicine using communication system.

SUMMARY OF INVENTION

This invention has five aspects:
1. A mechanism to create sound with the particular characteristics.
2. A mechanism to transmit the sound into the human body at the given anatomical surface area, example: At the right 5th inter-costal space on mid clavicular line.
3. A system to pick up or receive the resonated sound.
4. Software to do audiometric analysis.
5. A display to display the results based on the audiometric analysis of resonated sound.

In the first aspect of the invention there is a mechanism to create a sound of the particular characteristics In one form of this invention there is a mechanism to create the percussion sounds of the particular characteristics In another form of this invention a mechanism to produce the percussion sounds can be done using an electric motor and a tapping lever with a hammer as shown in FIG. 1. In this embodiment, this figure also shows the mechanism to transmit the sound into the human body at the given surface, a mechanism to pick up or receive the resonated sound using a microphone, an audiometric analyser and a display to display the results based on the audiometric analysis of resonated sound.

Yet in another form of this invention, the mechanism to produce the percussion sounds can be done using the torsion spring to store the energy reserve that turns the gears which moves the lever with hammer. This torsion spring can be manually powered.

Yet in another form of this invention the mechanism to produce the percussion sounds can be done using a hollow induction coil and an iron rod fitted with the hammer that moves inside the hollow induction coil up and down, and strikes the base to create a sound when the electric current is passed into the induction coil intermittently.

Yet in another form of this invention the mechanism to produce the percussion sounds can be done using a hollow electromagnetic coil and an iron rod which acts as a shaft, fitted with the hammer moves inside the hollow induction coil up and down, and strikes the base to create a sound when the electric current is passed into the induction coil intermittently.

Yet in another form of this invention the sound producing mechanism uses vibrator to produce sound.

Yet in another form of this invention the mechanism to produce the percussion sounds can be done using a spring system with the lever fitted with the hammer along with locking and releasing system to create sound.

Yet in another form of this device, a diaphragm can be placed firmly on the given surface of the body to pick up the resonated sound and vibrations whose signals are amplified for audiometric analysis.

Yet in another form of this device, it uses dedicated software to diagnose cardiovascular diseases.

Yet in another form of this device, it uses dedicated software to use in Oncology practice.

Yet in another form of this device, it uses dedicated software to diagnose Hepatic diseases and conditions.

Yet in another form of this device, it uses dedicated software to use in Obstetrics and Gynaecology practice.

Yet in form of this device, it uses dedicated software to diagnose abdominal diseases and conditions.

Yet in another form of this device, a telecommunication system is included with this device to transmit the data which can be used in telemedicine and epidemiology.

Yet in another form of this invention this device can function as described in the above embodiments as a stand-alone or in combination with each other.

BRIEF DESCRIPTIONS OF DRAWING

FIG. 6A illustrates Table 1 showing the audiometric variations of percussion sounds recorded from a normal left lung (control) and a right lung (test) with tuberculosis in a subject with pulmonary tuberculosis.

FIG. 6B illustrates Table 2 showing the audiometric variations of percussion sounds recorded from a normal left lung (control) and a right lung (test) with tuberculosis in a subject with pulmonary tuberculosis.

Figure 7:
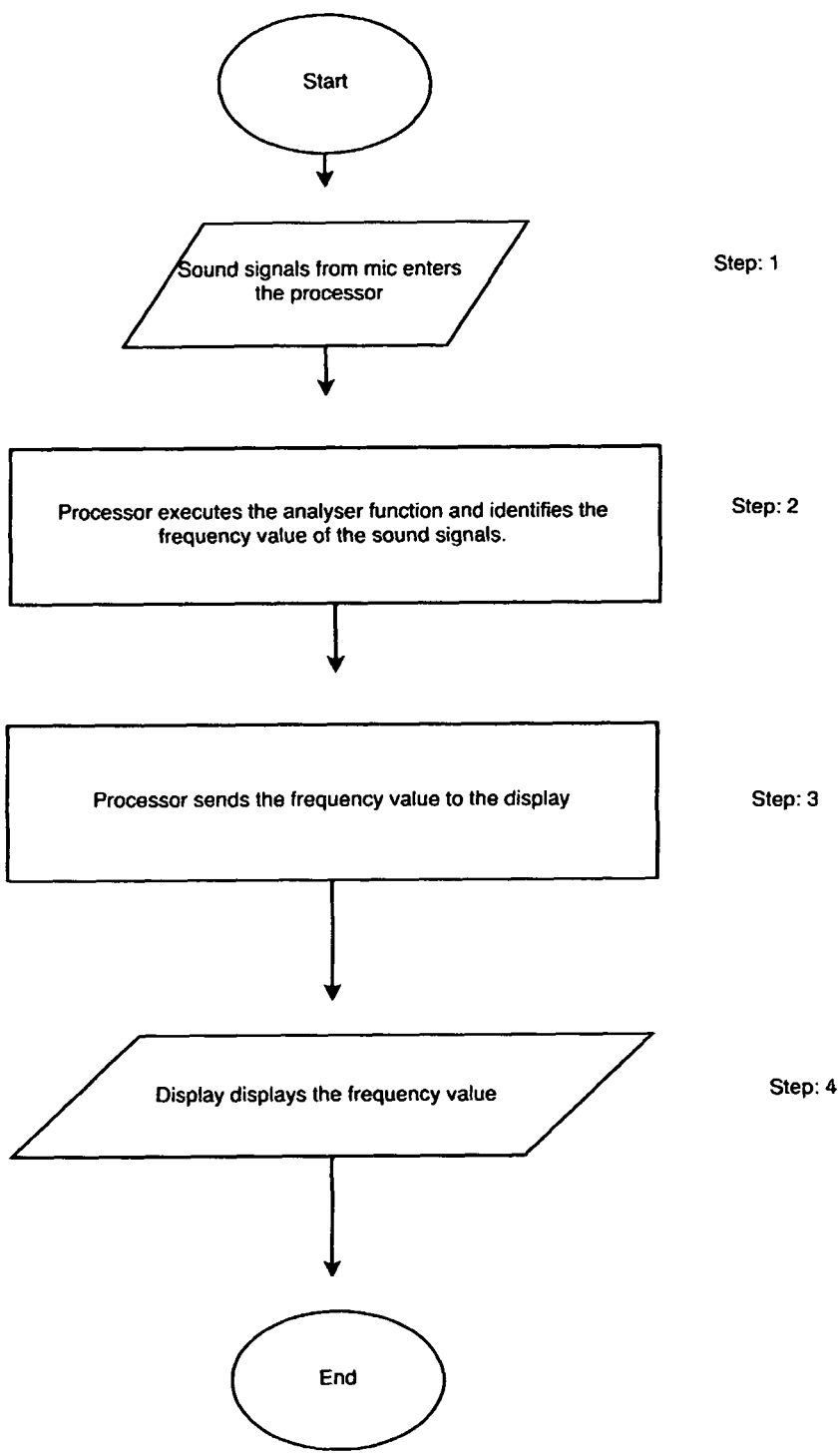

FIG. 7 exemplarily illustrates a flowchart showing the working of the non-invasive diagnostic device.

Figure 8:
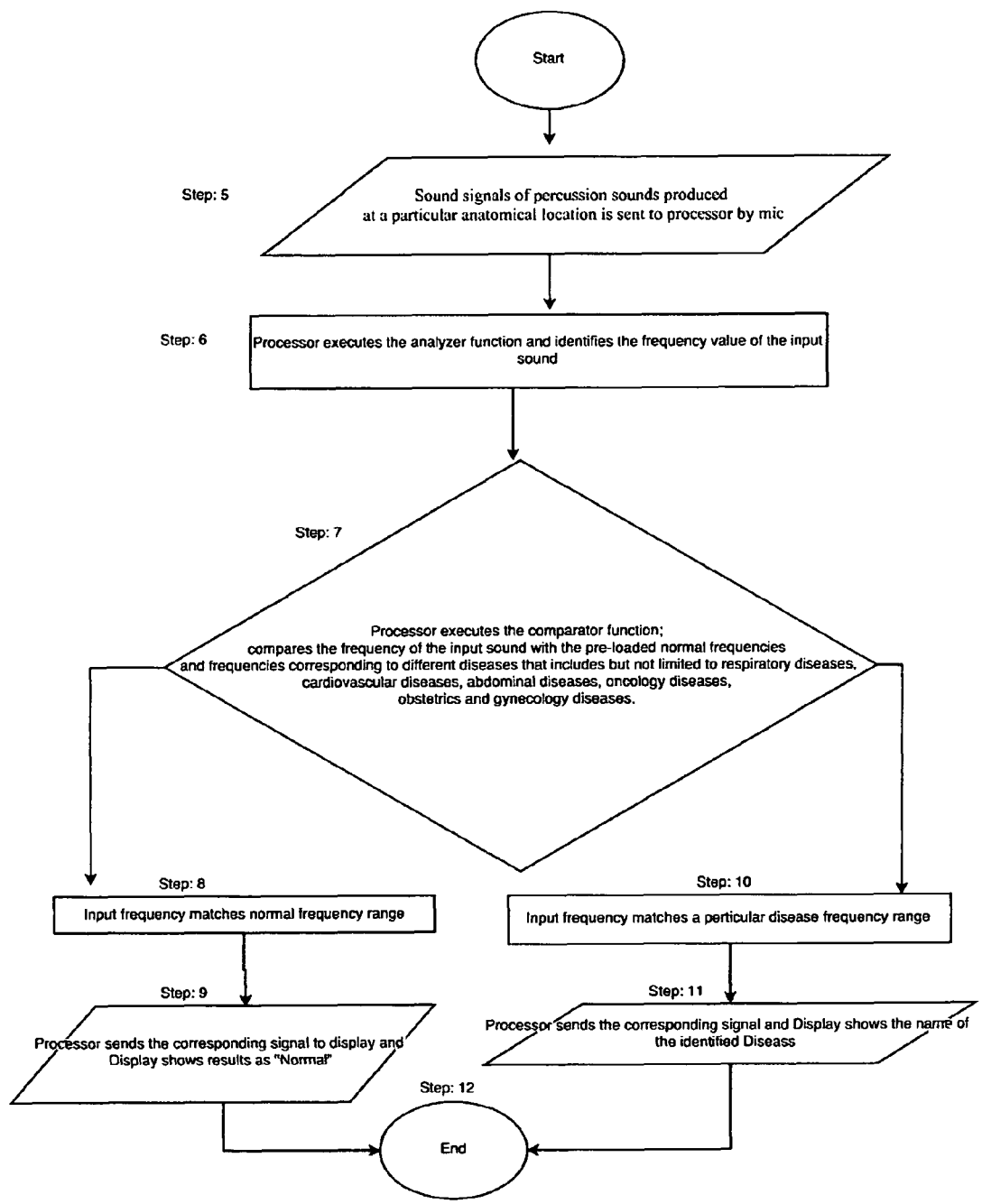

FIG. 8 exemplarily illustrates a flowchart showing the working of the non-invasive diagnostic device.

Figure 9:
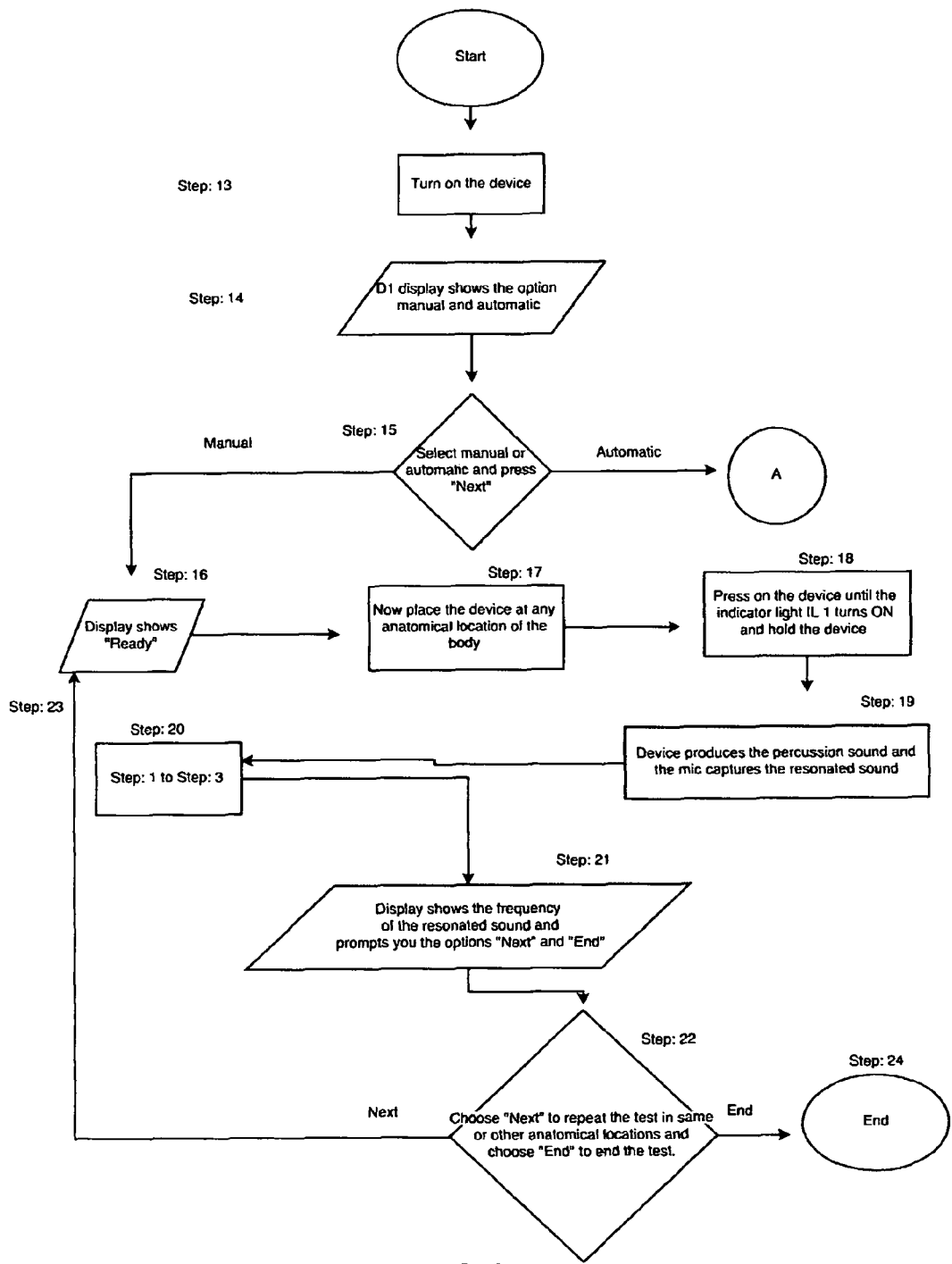
Figure 9:
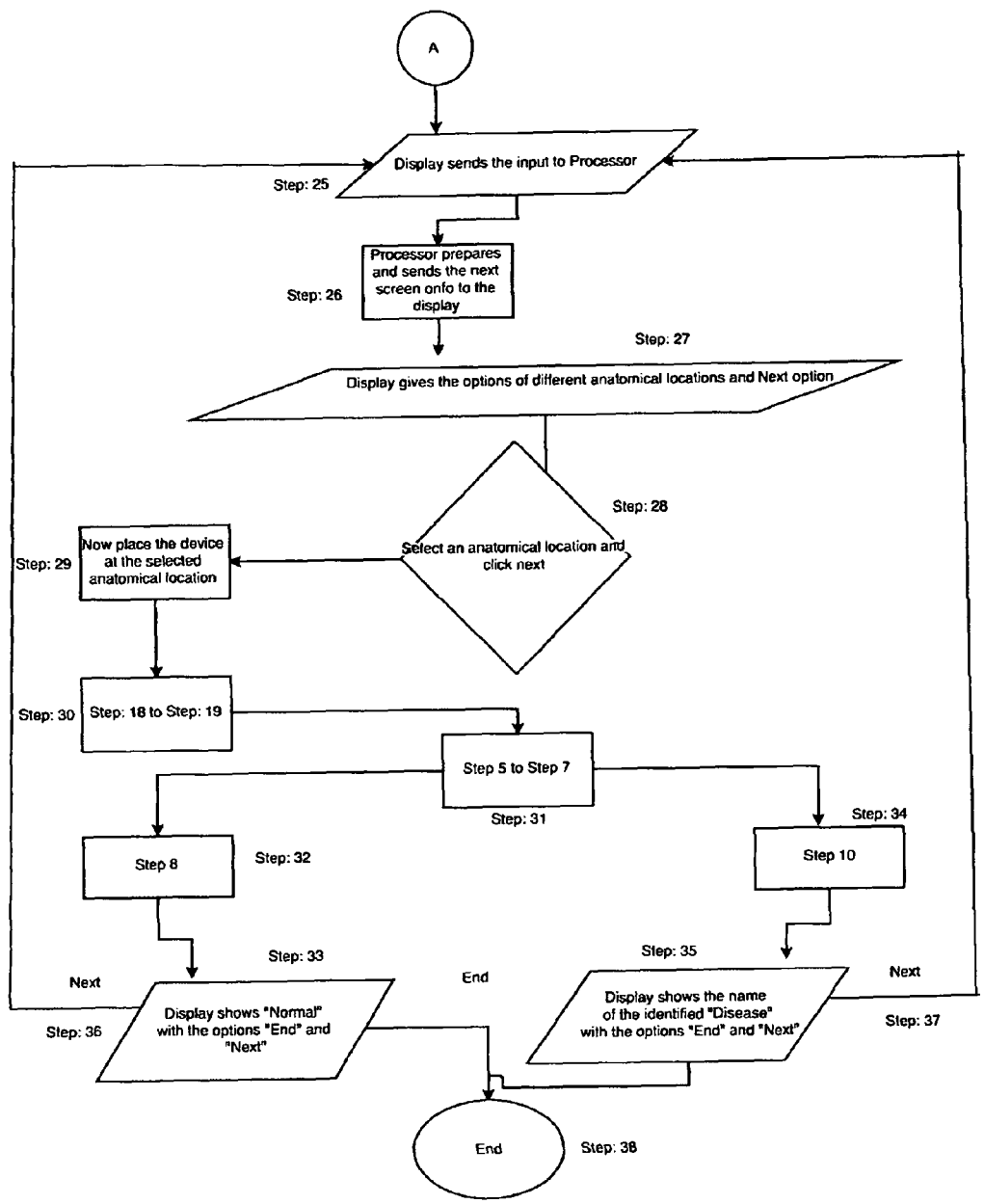

FIG. 9 exemplarily illustrates a flowchart showing the working of the non-invasive diagnostic device in manual and automatic modes.

DETAILED DESCRIPTION OF THE PREFERRED EMBODIMENTS

Figure 1:
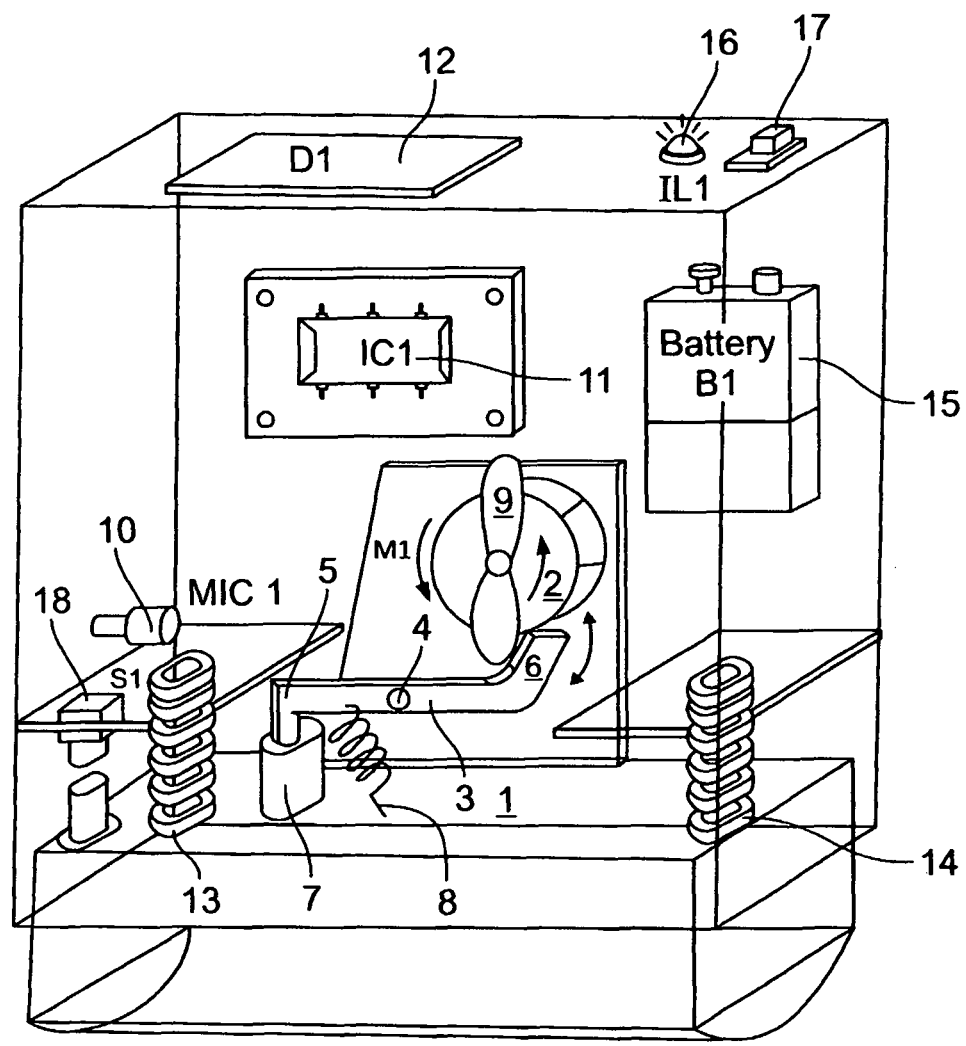
FIG. 1 shows the mechanism of the device with its different components.

In the first aspect of the invention there is a mechanism to create a sound of the particular characteristics In some embodiment of this invention there is a mechanism to create the percussion sounds of the particular characteristics In one of the embodiments of this invention a mechanism to produce the percussion sounds can be done using an electric motor and a tapping lever with a hammer as shown in FIG. 1. In this embodiment, this figure also shows the mechanism to transmit the sound into the human body from the given surface, a mechanism to pick up or receive the resonated sound using a microphone, an audiometric analyser and a display to display the results based on the audiometric analysis of resonated sound. The sound waves produced in the present invented device is based on medical percussion technique which has the audible sound frequency ranging from 20 Hz to 20,000 Hz.

In another embodiment of this invention, the mechanism to produce the percussion sounds can be done using the torsion spring to store the energy reserve that turns the gears which moves the lever with hammer. This torsion spring can be manually powered.

Yet in another embodiment of this invention the mechanism to produce the percussion sounds can be done using a hollow electromagnetic coil and an iron rod which acts as a shaft, fitted with the hammer moves inside the hollow induction coil up and down, and strikes the base to create a sound when the electric current is passed into the induction coil intermittently.

Yet in another embodiment of this invention the mechanism to produce the vibrating sounds with the particular characteristics can be done using a hollow electromagnetic coil and an iron rod fitted with the hammer that moves inside the hollow induction coil up and down, and strikes the base to create a sound when the electric current is passed into the induction coil continuously.

Yet in another embodiment of this invention the sound producing mechanism uses vibrator to produce sound.

Yet in another embodiment of this invention the mechanism to produce the percussion sounds can be done using a spring system with the lever fitted with the hammer along with locking and releasing system to create sound.

Yet in another embodiment of this device, a diaphragm can be placed firmly on the given surface of the body to pick up the resonated sound and vibrations whose signals are amplified for audiometric analysis.

Yet in another preferred embodiment of this device, a telecommunication system is included with this device to transmit the data which can be used in telemedicine and epidemiology.

Yet in another preferred embodiment of this device, it uses dedicated software to diagnose cardiovascular diseases.

Yet in another preferred embodiment of this device, it uses dedicated software to use in Oncology practice.

Yet in another preferred embodiment of this device, it uses dedicated software to diagnose Hepatic diseases and conditions.

Yet in another preferred embodiment of this device, it uses dedicated software to use in Obstetrics and Gynaecology practice.

Yet in another preferred embodiment of this device, it uses dedicated software to diagnose abdominal diseases and conditions.

Yet in another embodiment of this invention this device can function as described in the above embodiments as a standalone or in combination with each other.

Yet in another preferred embodiment of this device, it can also be connected to the external power source that can replace the battery function.

Yet in another preferred embodiment of this device, power switch can also be included in all the variants of this device to turn ON and turn OFF the device.

One of the preferred embodiments is described in FIG. 1 using the electrical motor FIG. 1 shows the arrangements of different components and the mechanism of the device. It has got the planar sliding base 1 which substitutes the finger in a manual percussion technique which is pressed firmly on the body of the subject. Upon Base 1, Motor 2 (M1) and the Lever 3 is mounted with the pulley 4 in the middle. Base 1 got two surfaces; inner and outer surface. Lever 3 got two ends; end 5 and end 6. These two ends 5 and 6 move up and down like a see saw. At end 5, a hammer 7 which substitutes the tapping finger in manual percussion technique is fitted. Motor 2 is fitted with the twin blade 9 that pushes down the end 6 of the lever 3. While the end 6 is pushed down, it pushes the other end 5 of the lever upwards against the tension of the spring 8. Once the rotating blade releases the end 6 of the lever, hammer 7 strikes the inner surface base 1 creating the percussion sound which is transmitted through the body of the subject when the device is pressed on the body of the subject in such a way the outer surface of base 1 comes in contact with the skin. The force with which the hammer 7 taps on the base 1 depends on the tension of the Spring 8. Resonated percussion sound signals are sent by the Microphone 10 (Mic1) which is mounted near the hammer 7 to the Processor 11 (IC1). Processor 11 is programmed in a way to analyse the audiometric variations of these sound signals and sends the output to display 12 (D1). Sliding planar base 1 slides up and down to a limited distance against the tension of the springs 13 and 14. This spring system 13, 14 determines the adequate force given over the device when pressed on the skin of the subject at the predefined anatomical locations like supra-clavicular, clavicular, infra-clavicular, intercostals spaces, supra-scapular, scapular, infra-scapular, auxiliary regions of the body.

This spring arrangement 13, 14 together with the predefined material of hammer 7, base 1, press switch 18 and tension of spring 8 help in creating the standard percussion sounds which will vary depending on the disease conditions. Indicator green light 16 gets illuminated when press switch 18 is activated by applying adequate force while pressing the device on the body of the subject against the spring system 13, 14. Switch 17 is used to activate the Motor 2 which can be turned on before the press switch 18 gets activated that enables automatic mode. This device also has a battery 15 for power supply. The device can also be connected to the external power source that can replace the battery function. A power switch can also be included in all the variants of this device to turn ON and turn OFF the device.

Figure 2:
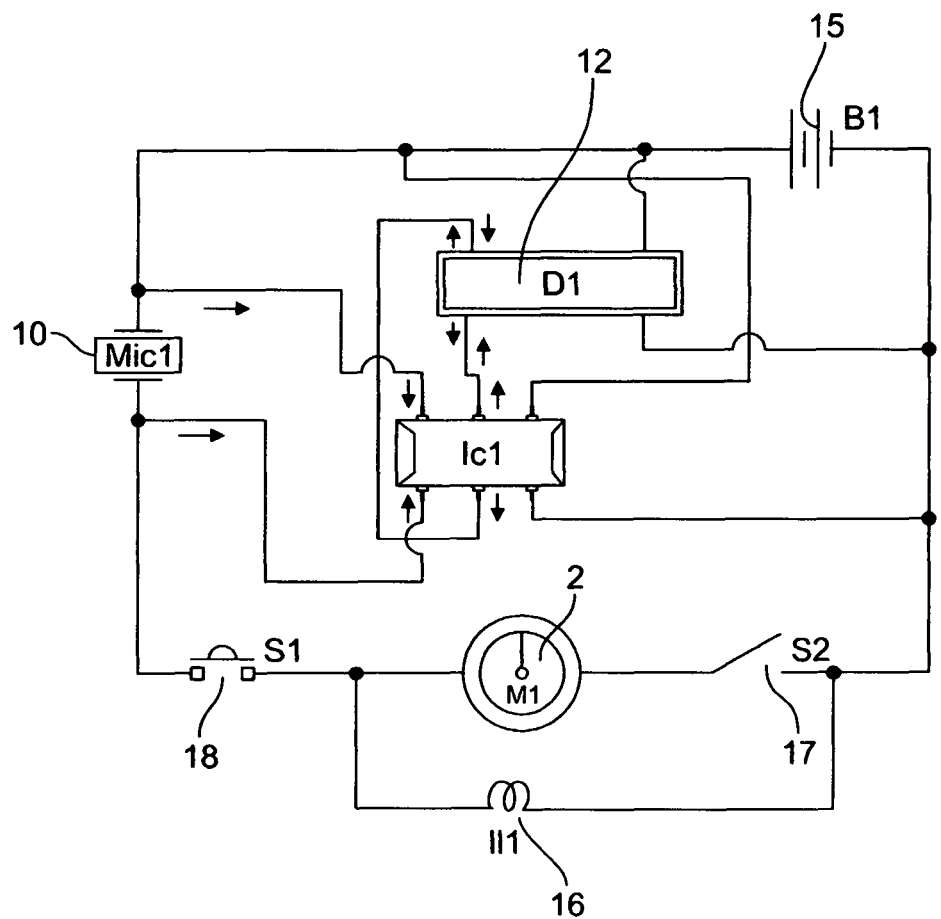
FIG. 2 is the circuit diagram showing different components of this device.

FIG. 2 is a circuit diagram of the proposed handheld device. Motor 2 (M1) is inhibited by press switch 18 (S1) and switch 17 (S2). S1 press switch is activated when the adequate force is applied over the device while pressing upon the body of the subject at predefined anatomical locations. Once the press switch 18 (S1) is activated indicator green light 16 (IL1) gets illuminated after which by enabling the switch 17 (S2) motor 2 (M1) is activated. Switch 17 (S2) can also be turned on in advance before the press switch 18 (S1) gets activated. The circuit has a processor IC1 which receives the signals from microphone 10 (Mic 1). The function of this processor is to record, analyse the audiometric variations of different percussion sounds produced in subjects thereby differentiating the normal variations and the sound variations produced in different disease conditions and send output signals to the display 12 (D1) which displays the results. Depending on these variations, the processor 11 (IC1) analysis and compares the data and produces test results on the display. The algorithm to program this processor function is presented. The considerations of audiometric variations may include pitch, loudness, quality, frequency and other measurable qualities of sound. This circuit also has a battery 15 (B1) for power supply.

Figure 3:
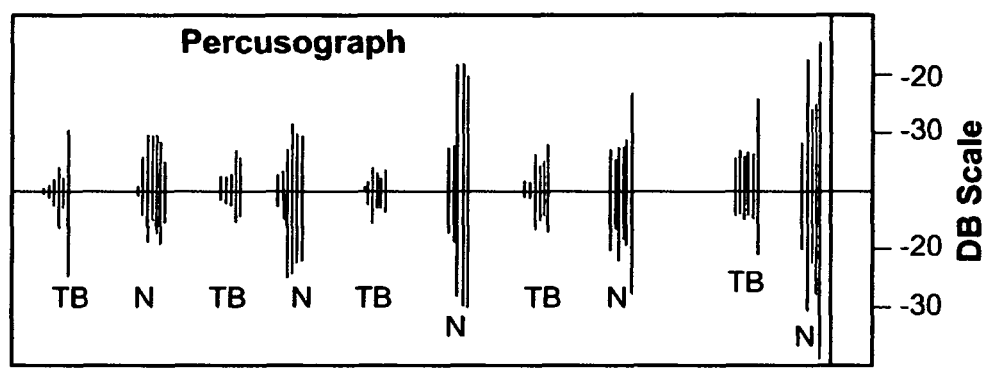
FIG. 3 is an audiometric graph of percussion sounds (Percusograph) obtained in a subject with right pulmonary tuberculosis

In another form of using this technology, FIG. 3 shows the Computerised Percusograph (audiometric graph of percussion sounds obtained by analysing in computer) of percussion sounds produced in the subject with pulmonary tuberculosis on his right lung. TB is the waves produced by the percussion sounds through resonance of right lung with tuberculosis and N is the waves produced by the percussion sounds through resonance of normal left lung. The difference in terms of the decibels in two different set of waves TB and N of this graph should be noted. The proposed term for this form of technology is Percusography, the proposed term for the graph obtained in this method is Percusograph and the term for the proposed dedicated electronic equipment is Percusogram.

Figure 4:
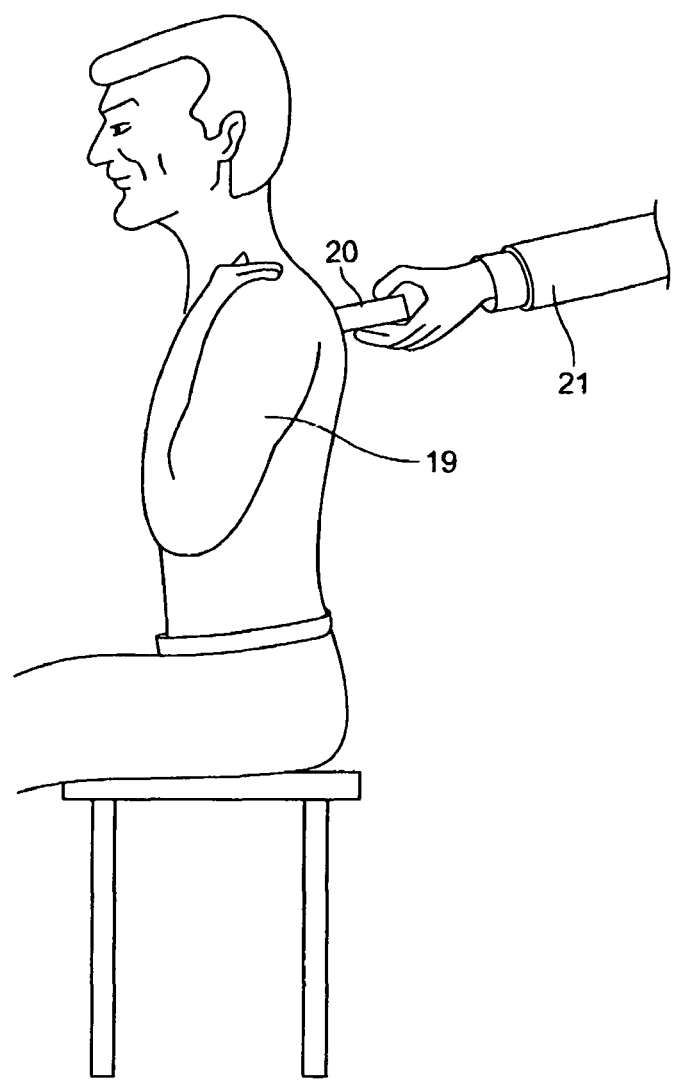
FIG. 4 shows the application of this device on a subject by a doctor/technician.

FIG. 4 shows the application of this device 20 on a subject 19 sitting in an up-right position by a doctor/technician 21.

Figure 5:
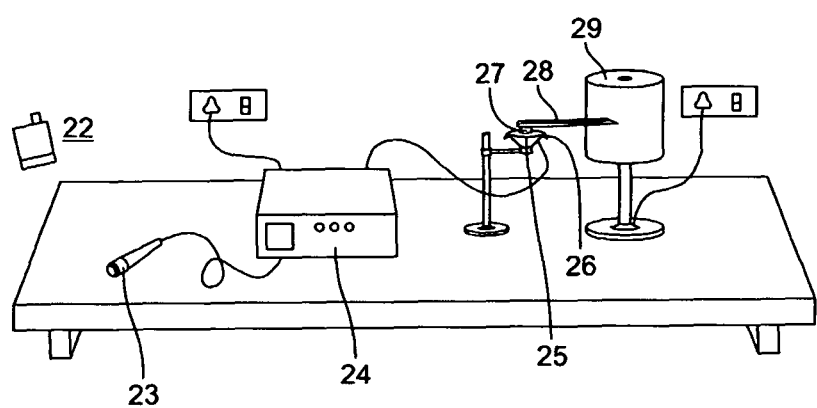
FIG. 5 shows the basic form of this invention

FIG. 5 shows the basic form of recording the audiometric graphs (Percusographs) of percussion sounds. Percussion sounds from the basic tapping unit 22 (which is a handheld device without processor and display but capable of producing standard percussion sounds) are recorded and amplified by an amplifier 24 through a microphone 23 and sent to speaker 25 which is mounted on a stand. There is sheet of latex 26 covered over the speaker such that it vibrates depending on the sound produced by the speaker. These vibrations are recorded on the moving graph like smoke drum 29 by a pointer 28 which is fitted to a cork 27 and mounted on the latex sheet 26 covering the speaker 25.

In FIG. 6A, Table 1 shows audiometric variations of the loudness in decibels units of resonated sounds produced by the normal left lung (N) VS the resonated sounds produced by the right lung with tuberculosis (TB) in a patient with tuberculosis. These sounds were recorded with consent through manual percussion technique performed on the chest wall at the 5th, 6th and 7th Intercostal spaces at the midclavicular line which is around the affected area of lung, as a part of clinical examination from a 60-year-old tuberculosis patient as diagnosed by clinical presentation, sputum analysis and x-rays. Recorded percussion sounds are analysed in a sound analyser.

In FIG. 6B, Tablet shows the frequency variations of resonated sounds produced by the normal left lung (N) VS the resonated sounds produced by the right lung with tuberculosis (TB) in a patient with tuberculosis. These sounds were recorded with consent through manual percussion technique performed on the chest wall at the 5th and 7th Intercostal spaces at the midclavicular line which is around the affected area of lung, as a part of clinical examination from a 60-year-old tuberculosis patient as diagnosed by clinical presentation, sputum analysis and x-rays. Recorded percussion sounds are analysed in a sound analyser.

FIG. 7 exemplarily illustrates a flowchart for programming the microprocessor to identify the frequency of percussion sound. FIG. 8 exemplarily illustrates a flowchart for programming the microprocessor to execute diagnostic function. On starting the device, a test frequency is captured by the microphone of the device as described in FIG. 1. The processor within the device compares the test frequency with pre-loaded normal frequency ranges. If the test frequency lies within the normal frequency ranges that have been preloaded into the device, the device displays the result as "Normal". In case the test frequency does not lie within the normal frequency ranges, the processor begins comparing the test frequency with frequency ranges of a disease 1, for example, tuberculosis. This frequency range of the disease 1 (tuberculosis) is also pre-set based on data received from experimental tests done on individuals affected by tuberculosis. Similarly, frequency ranges of multiple diseases may be stored in the device. The processor keeps comparing the test frequency to the different frequency ranges of different diseases until a match is found. If no match is found, the device displays the result as "abnormal". On finding the match, the device displays the result as the corresponding disease which has a frequency range matching the test frequency.

FIG. 9 exemplarily illustrates a flowchart showing the working of the non-invasive diagnostic device in manual and automatic modes.

I claim:

1. A non-invasive device to diagnose a medical condition of a patient based on audiometric analysis of resonated sound comprising:
   i. a sound generation assembly comprising:
      a base comprising an inner surface and an outer surface, the outer surface of the base configured to contact a predefined anatomical surface area of a human body, wherein the inner surface is configured to contact a press switch based on the predefined anatomical surface area exerting an applied force on the outer surface exceeding a resisting force supplied by one or more spring elements attached to the inner surface of the base;
      a lever comprising a first end, a second end, and a spring element, the lever mounted on a pulley at a middle section of the lever, wherein the first end and second end are configured to move in an upward direction and a downward direction, wherein the first end is configured to contact rotating blades of a motor to move in the downward direction, wherein the second end is configured as a hammer to contact the inner surface of the base to generate sound, and wherein the spring element restrains motion of the lever;
   a microphone positioned proximal to the lever to receive the resonated sound from the human body, wherein the microphone transmits the received resonated sound to a processor; and
   the processor configured to execute a set of instructions to:
      receive the resonated sound from the microphone;
      compare the resonated sound from the microphone with a first resonated sound generated from a healthy human body;
      analyze the medical condition of the patient based on audiometric variations of the resonated sound differing from the first resonated sound; and
      display the analyzed audiometric variations of the resonated sound.

2. The non-invasive device as claimed in claim 1, wherein the processor is further configured to compare the resonated sound with sample resonated sounds generated by bodies affected by respiratory diseases, cardiovascular diseases, hepatic diseases, and abdominal diseases to diagnose respiratory disease, cardiovascular disease, hepatic disease, and abdominal disease in the human body.

3. The non-invasive device of claim 1, further comprising a switch configured to supply power to the motor for rotating the blades of the motor.

4. The non-invasive device of claim 1, wherein the audiometric variations of the resonated sound are audiometric variations in one or more of a pitch, a loudness, a frequency, a wavelength, and other measurable quantities of the resonated sound.

5. The non-invasive device of claim 1, wherein the predefined anatomical surface area of the human body is selected from the group consisting of a supra-clavicular area, a clavicular area, an infra-clavicular area, intercostal spaces, supra-scapular area, and an infra-scapular area.

6. The non-invasive device of claim 1, wherein the sound generated by the sound generation assembly is modifiable based on adjusting one or more of a tension supplied by the one or more spring elements, a material of the second end of the lever, and a material of the base.

* * * * *